United States Patent [19]

Alt et al.

[11] 4,094,661

[45] June 13, 1978

[54] PLANT GROWTH REGULATORS

[75] Inventors: Gerhard H. Alt, Creve Coeur; John E. Franz, Crestwood, both of Mo.

[73] Assignee: Monsanto Company, St. Louis, Mo.

[21] Appl. No.: 705,316

[22] Filed: Jul. 14, 1976

Related U.S. Application Data

[62] Division of Ser. No. 536,675, Dec. 26, 1974, Pat. No. 3,985,773.

[51] Int. Cl.$^2$ .............................................. A01N 9/28
[52] U.S. Cl. ........................................... 71/88; 71/76
[58] Field of Search ...................................... 71/88, 76

[56] References Cited

U.S. PATENT DOCUMENTS

| 2,811,535 | 10/1957 | Wheeler et al. | 71/88 X |
| 2,838,522 | 6/1958 | Wheeler et al. | 71/88 X |
| 2,945,865 | 7/1960 | Wheeler et al. | 71/88 X |
| 2,995,577 | 8/1961 | Sauers et al. | 71/74 X |
| 2,997,481 | 8/1961 | Wheeler et al. | 71/88 X |
| 3,035,065 | 5/1962 | Sauers et al. | 71/75 X |
| 3,041,376 | 6/1962 | Sauers et al. | 71/88 X |

*Primary Examiner*—Joseph Paul Brust
*Attorney, Agent, or Firm*—William I. Andress; Donald W. Peterson

[57] ABSTRACT

The disclosure herein pertains to the use of certain 3-[(naphthyl, or substituted-phenyl)imino]-phthalides, some of whose members are novel, to regulate the natural growth or development of plants.

14 Claims, No Drawings

PLANT GROWTH REGULATORS

This is a division of application Ser. No. 536,675 filed 12/26/74 now U.S. Pat. No. 3,985,773, issued Oct. 12, 1976.

BACKGROUND OF THE INVENTION

1. Field of the Invention

In one embodiment, the invention herein pertains to the field of plant growth regulation.

In another embodiment, this invention pertains to the use of plant growth regulator compositions containing certain 3-[(naphthyl, or substituted-phenyl)imino]-phthalides, among which are novel compounds per se.

2. Description of the Prior Art

Within the prior art pertinent to this invention is disclosed a broad generic class of compounds encompassing species pertinent to the present invention. These compounds, prepared by known methods, are variously described generically as 3-substituted imino phthalides or N-(substituted) phthalisoimides. See, e.g., an article by W. R. Roderick et al in J. Org. Chem. 28, 2018–24 (1963) and in the same journal an article by R. K. Howe at 38, 4164–67 (1973).

Although the prior art discloses numerous imino phthalides having no substituents or a variety of substituents on the phenyl moiety of the aniline residue, including halo, methyl, alkoxy and dimethylaminophenyl radicals, to applicants' knowledge, the compounds 3-[(o-chloro-m-trifluoromethylphenyl)imino]-phthalide and 3-[(o,m-dimethoxyphenyl)imino]-phthalide are novel and unobvious.

The prior art appears silent with respect to any suggested use of imino phthalides as plant growth regulators. In fact, applicants have discovered that certain of the known imino phthalides are inactive as plant growth regulators. For example, the unsubstituted phenyl imino phthalide and those phthalides substituted with p-chlorophenyl, p-methoxyphenyl, o-ethoxyphenyl and dimethylaminophenyl radicals are all inactive. Hence, without guidance from the prior art, applicants have found that certain imino phthalides are effective plant growth regulators, and further, with respect to those species having halogen or alkoxy substituents, the position of these radicals on the phenyl ring is critical.

Other prior art related to the present invention in a general sense includes isomaleimides disclosed in U.S. Pat. Nos. 2,995,577 and 3,035,065, to C. K. Sauers et al and other compounds described as substituted anilino phthalides as disclosed in U.S. Pat. No. 2,945,865 to D. D. Wheeler et al. However, none of the Sauers et al or Wheeler et al compounds are within the scope of the invention disclosed and claimed herein.

SUMMARY OF THE INVENTION

This invention in its various embodiments relates to the regulation of plant growth or development by applying to the plants a composition containing an effective amount of a compound having the formula

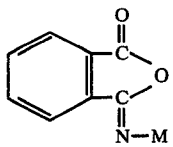

wherein M is selected from the group consisting of naphthyl, tolyl, o- and m-monohalo- and dihalophenyl, o, m-dimethoxyphenyl and o-halo-m-trifluoromethylphenyl radicals.

Within the above class of compounds, it has been found that the compound having said o, m-dimethoxyphenyl radical is both novel and has particular application as a plant growth regulator with respect to monocotyledonous plants typified by corn, whereas the other compounds within the above formula, among which the compound having the o-halo-m-trifluoromethyl radical is novel, have particular application with respect to dicotyledonous plants typified by soybeans, tomatoes and cotton

DETAILED DESCRIPTION OF THE INVENTION

In accordance with this invention a method is provided whereby viable plants are treated with a chemical substance which alters their natural growth or development to enhance the various agricultural or horticultural features of the plants. As employed herein, the term "natural growth or development" designates the normal life cycle of the plant in accordance with its genetics and its environment, in the absence of artificial, external influences.

The method of regulating plant growth provided by this invention is particularly useful for treating dicotyledonous and monocotyledonous plants to modify the vegetative growth, the flowering or fruit set or to optimize the yield. Representative dicotyledonous crop plants which may be treated with the compounds of this invention include the legumes, for example, soybean, cotton, beans, coffee, tomato, peas and the like, which often do not obtain their yield capacity due to premature blossom drop or because of failure of the fruit to set. Representative monocotyledonous plants include cereal or grain fruit crops such as corn, wheat, barley, oats, rye and sorghum.

For convenience, the term "active ingredient" will be used hereinafter to denote one or more of the 3-substituted imino phthalides as previously defined.

It is to be understood that the regulation of natural growth and development does not include killing or herbicidal action. Although phytotoxic or lethal amounts of the active ingredient might be employed to destroy certain plants, it is contemplated here to employ only such non-lethal amounts of said active ingredient as will serve to regulate the natural growth and development of useful plants without substantial injury. As may be expected and as long understood by those skilled in the art, such effective plant regulating amounts will vary, not only with the particular active ingredient selected for treatment, but also with the regulatory effect to be achieved, the species of plant being treated and its stage of development, and whether a permanent or transient regulating effect is sought. Other factors which may bear upon the determination of an appropriate plant regulating amount include the plant growth medium, the manner in which the treatment is to be applied, weather conditions such as temperature or rainfall, and the like.

In accordance with the instant invention it has been found that desirable regulation of natural plant growth or development is achieved by application of the active ingredient to plants in various stages of development. Accordingly, in the practice of this invention the active ingredient can be applied to the soil habitat of the plant or directly to the plant in the seedling stage, flowering stage or fruiting stage and the like or can be applied sequentially to plants at more than one stage of development. Such application may be made directly to one or more of the plant's parts, such as stems, leaves, flowers, fruit or the like. Generally, the application is made by spraying the plants using conventional techniques.

Regulation of the natural growth or development of plants by chemical treatment results from the effect of the chemical substance on the physiological processes of the plant and the effect of such substance may be manifested by the morphology of the plant. As should be readily apparent, said regulation may also result from a combined or sequential effect of the chemical manifesting a response in both physiology and morphology.

In general, regulation of the natural growth or development which leads to a morphological change in the plant is readily noticeable by visual observation. Such changes can be found in the size, shape, color or texture of the treated plant or any of its parts. Similarly, changes in the quantity of plant fruit or flowers can be simply noted.

On the other hand, regulation which leads to changes only in the physiological processes occur within the treated plant and are usually hidden from the eye of an observer. Changes of this type are most often in the production, location, storage or use of naturally occurring chemicals, including hormones, within the plant. Physiological changes in a plant often are recognized when followed by a subsequent change in morphology. Additionally, there are numerous analytical procedures known to those skilled in the art for determining the nature and magnitude of changes in the various physiological processes.

The individual compounds of the instant invention serve to regulate the natural growth or development of treated plants in a number of diverse ways, and it is to be understood that each compound may not produce identical regulatory effects on each plant species or at every rate of application. As stated above, responses will vary in accordance with the compound, the rate, the plant, etc.

A regulatory response demonstrated by the compounds useful in the practice of this invention can be generally termed retardation of vegetative growth and such a response has a wide variety of beneficial features. In certain plants this retardation of vegetative growth causes a diminution or elimination of apical dominance leading to a shorter main stem and increased lateral branching. This regulation of the natural growth or development of plants produces smaller, bushier plants which often demonstrate increased resistance to the climatic extremes, pest infestations and the like. Thus, the method of this invention provides for plants that are in a good state of health and tends to produce more vigorous plants.

As illustrated in the treatment hereinafter presented, the individual compounds of this invention regulate the natural growth or development of treated plants in numerous other and different respects. Included among these other regulatory effects are the inducing of axillary bud development, the alternation of shape and canopy, the delay or acceleration of fruit or pod set, etc. Although regulatory effects such as those described above can be desirable, often it is the ultimate result of these effects upon the economic factor which is of primary significance in crop plants or upon the aesthetic factor in ornamental plants. Thus, it must be recognized that increases in yield of individual plants, increases in the yield per unit of cropping area, improvement in the quality of the plants' product, improvement in the plants vigor and reductions in the cost of harvesting and/or subsequent processing are all to be considered in any assessment of the consequence of an individual regulatory effect during the growth or development of a plant.

The practice of the method of this invention is particularly useful for improving the efficiency of dicotyledonous row crops such as soybean, tomatoes and cotton, and monocotyledonous crops such as corn. The application of the compounds of this invention to such growing crop plants often reduces the stature of the plants without the expected substantial reduction in seed yield. In this manner the plant's efficiency of production is improved and a means is provided for optimizing the crop by increasing the plant population per unit area and treating said crop with the active ingredient during its growing stage. Such reduction in plant stature also increases accessibility to the field for other treatments, cultivation and harvesting.

One aspect of this invention is the provision of a plant growth regulating composition comprising an effective plant growth regulating amount of the 3-substituted imino phthalide compounds described above and an adjuvant.

The plant growth regulating compositions are particularly effective for practicing the method of regulating the natural growth or development of plants provided by this invention. In view of the activity of the active ingredients at low rates of application, it is desirable to use compositions comprising an effective amount of the active ingredient and an adjuvant to facilitate a uniform distribution of the compound on the plants. Adjuvant, as used herein, includes one or more materials in liquid or solid form. Thus, suitable adjuvants are diluents, extenders, carriers, surfactants, foaming agents, conditioning agents, solvents and, usually, combinations thereof. The compositions can be in numerous forms, such as, dusts, powders, water soluble powders, wettable powders, solutions, foams, dispersions or emulsions. Generally, it is preferred to use one or more surfactants in the plant growth-regulating compositions which aid in wetting the treated plant surface and for providing stable dispersions of the active ingredient in various inert carriers or diluents in the composition or added to the composition prior to application to the plants. Suitable surfactants which can be employed in the compositions of this invention are well known surface active agents, such as, wetting agents, emulsifiers, dispersing agents and can be nonionic, anionic or cationic. Preferred surfactants are the nonionic or the anionic type which are widely used in compositions employed in agronomic treatments. Representative nonionic surfactants are polyoxyethylene esters of fatty acids, octylphenyl polyethylene glycol ethers, polyoxyethylene derivatives of long-chain alcohols and the like. Representative anionic surfactants are alkali and alkaline earth salts of alkylarylsulfonic acids such as sodium lauryl sulfonate, dialkyl sodium sulfosuccinate esters and the like. Such surfactants are well known and reference is made to U.S. Pat. No. 2,547,724 for detailed examples of same.

Usually the plant growth-regulating compositions of this invention take the form of a concentrate which can be readily extended with an inert carrier prior to application to the plants. Said concentrates in liquid form generally consist of a solvent, surfactant, emulsifier, defoamer and/or other additive and about 25 to 75% by weight of the active ingredient. These liquid concentrates can be diluted with water to provide a composition, suitable for application to plants, which contain from about 0.1 to about 15%, and commonly from about 1.0 to 10%, by weight of the active ingredient. Concentrates in solid form are, for example, water soluble powders consisting of finely divided solids such as calcium silicate, surfactant and from about 5 to 80% or more by weight of the active ingredient which are diluted with water prior to applying to the plants. Broadly, the plant growth regulator compositions herein may contain 0.1 to 80% or more by weight of the active ingredient. These compositions may be applied at rates of from 0.05 to 20 lb/acre or more, a preferred range being from 1.0–10 lb/ac., as more particularly detailed below.

In selecting the appropriate non-lethal rate of application of the active ingredient, it will be recognized that precise dosages will be dependent upon the plant species being treated, the particular plant part or habitat to which application is made, the development stage of the plant, the particular chemical employed, the mode of application and various other factors known to those skilled in the art. In foliar treatment for the regulation of plant growth, the active ingredients are applied in amounts from about 0.05 to about 10 or more pounds per acre. Foliar applications of from 0.1 to 6 pounds of the active ingredient per acre are preferred. In applications to the soil habitat of the plants the active ingredients are applied in amounts of from about 0.01 to about 20 pounds per acre or more. Preferably, the active ingredients are applied to the soil at a rate of from 0.1 to 10 pounds per acre, and in particular embodiments at rates of from 1 to 6 lb/ac. Foliar application to plants at the blooming stage, e.g., 10% blossoms, are particularly advantageous and are preferred.

The 3-substituted-imino-phthalides of this invention are prepared by known methods. For example, the imino phthalides of interest may be prepared by dehydration of the corresponding phthalamic (or phthalanilic) acid with acetic anhydride (T. L. Fletcher et al, J. Org. Chem., 26, 2037 (1961), or with trifluoroacetic anhydride (Roderick et al cited above), or with dicyclohexylcarbodiimide in dichloromethane (methylene chloride); (R. J. Cotter et al, J. Org. Chem., 26, 10 (1961). The R. K. Howe article, supra, describes yet another method for preparing the imino phthalides herein. The foregoing literature references are incorporated herein by reference.

The 3-substituted-imino-phthalides herein are generally colored compounds and are characterized, in part, by a distinctive absorption in the I. R. spectrum at 5.54 $\mu$ and 5.88 $\mu$.

In specific working embodiments, the preparation of the novel compounds of this invention will be described in Examples 1 and 2 below. In all examples below the elemental analysis values are in percentages.

EXAMPLES 1

To a suspension of 2',5'-dimethoxyphthalanilic acid (0.02 mole) in methylene chloride (25 ml) was added dropwise with stirring N,N'-dicyclohexylcarbodiimide (0.02 mole) in methylene chloride. This mixture was stirred at room temperature for 3–5 hours, then filtered to remove dicyclohexylurea. The filtrate was evaporated at low temperature in vacuo to give 3-[(o, m-dimethoxyphenyl)imino]-phthalide. The product was crystallized from cold aqueous acetone to give analytically pure material in about 58% yield and having a melting point of 104°–107° C.

Anal. Calc'd for $C_{14}H_{18}Cl_1N_1O_2$: C, 65.26; H, 3.12 N, 5.44 Found: C, 65.11; H, 3.13; N, 5.27

EXAMPLE 2

By use of the identical procedure described in Example 1 and using the same quantities of the appropriate and corresponding reactants, 3-[(o-chloro-m-trifluoromethylphenyl)imino]-phthalide was prepared in about 46.3% yield and having a melting point of 120°–122° C.

Anal. Calc'd for $C_{15}H_7Cl_1F_3N_1O_2$: C, 56.32; H, 2.17; N, 4.30 Found: C, 56.44; H, 2.08; N, 4.40

EXAMPLE 3

This example describes an alternative preparation of the phthalides utilized in this invention by the dehydration of a phthalanilic acid with trifluoroacetic anhydride.

To a suspension 2'-chlorophthalanilic acid (0.02 mole) and triethylamine (0.025 mole) in dry dioxane (25 ml) was added trifluoroacetic anhydride (0.025). The reaction mixture was stirred at room temperature for 6–18 hours, then poured into cold water and the precipitate isolated by filtration. The product was recrystallized from acetone to give analytically pure material in 50.0% yield and having a melting point of 141°–143° C.

Anal. Calc'd for $C_{14}H_8Cl_1N_1O_2$: C, 65.26; H, 3.17; N, 5.44 Found: C, 65.11; H, 3.05; N, 5.27

Following the identical procedure described in Example 3, but substituting the appropriate phthalanilic acid, the corresponding phthalides were prepared and are further described in Examples 4–7 below.

EXAMPLE 4

3-[(m-chlorophenyl)imino]-phthalide
Yield: 50%
M.P.: 98°–100° C
Anal. Calc'd for $C_{14}H_8Cl_1N_1O_2$: C, 65,26; H, 3.13 Found: C, 65.28; H, 3.00

EXAMPLE 5

3-[(m, p-dichlorophenyl)imino]-phthalide
Yield: 32%
M.P.: 123°–125° C
Anal. Calc'd for $C_{14}H_7Cl_2N_1O_2$: C, 57.56; H, 2.42 Found: C, 57.85; H, 2.59

EXAMPLE 6

3-[(1-naphthyl)imino]-phthalide
Yield: 41.5%
M.P.: 134°–136° C
Anal. Calc'd for $C_{18}H_{11}NO_2$: C, 79.11; H, 4.06 Found: C, 79.15; H, 4.07

EXAMPLE 7

In accordance with the procedure described by R. K. Howe, supra, tributyl (3-phthalidyl)phosphonium bromide (0.020 moles) was reacted with 2-nitrosotoluene (0.020 mole) in 60 ml of methylene chloride, to which triethylamine (0.020 mole) was added dropwise with stirring at room temperature. The product, recovered in 82% yield, was a yellow solid, m.p. 136°–138° C, identified as N-(o-tolylimino)phthalimide. I. R. for this product (mineral oil mull) 5.51 (sh), 5.60 $\mu$, 5.88 $\mu$. Elemental analysis for this product from the literature (Roderick et al supra p. 2020) is as follows:

Anal. Calc'd for $C_{15}H_{11}NO_2$: C, 75.93; H, 4.67; N, 5.90 Found: C, 75.84; H, 4.49; N, 5.98

The useful and unexpected plant growth regulating properties of the imino phthalide compounds of this invention are demonstrated by exemplary tests set forth in the examples below.

In the following examples the chemical was applied as an aqueous composition at the equivalent rate of active ingredient indicated. The aqueous compositions were prepared by solubilizing the required amount of the chemical in a volume of solvent, e.g., acetone, which is further admixed with a like volume of 0.5% by weight aqueous solution of a suitable surfactant, e.g., polysorbitan monolaureate (Tween Twenty surfactant), to provide sufficient composition which is applied at the rate equivalent to 200 gallons per acre to apply the chemical at the equivalent rate indicated.

EXAMPLE 8

A number of soybean plants, representative of dicotyledonous plants, are grown from seed in aluminum pans in a greenhouse for a period of approximately 1 week to the primary leaf stage. The plants are thinned to three uniform plants in each pan and the height of each plant is measured to the terminal bud and the average height is noted. One pan containing three soybean plants is used for each chemical treatment and four pans are not treated and used as a control. The aqueous composition of the chemical is then applied to the pan of growing plants by overhead spray at an established rate expressed as pounds per acre. The treated pans along with the control pans are watered from below, fertilized and otherwise maintained in a greenhouse under uniform growth conditions. Two weeks after application of the chemical the average height of the plants in the treated pan is determined as above and the difference in the average height before and 2 weeks after application represents the development of the treated plants. This development in growth of the treated plants is compared to the average development in growth of the plants in the control pans during the same period of time. A variation of 25% or more in the development of at least two-thirds of the treated plants when compared to the development of the control plants demonstrates that the chemical is effective for regulating the natural growth or development of the plants. Accordingly, a chemical is considered effective when the treated plants manifest at least a 25% decrease in height development when compared to the untreated control plants, i.e., retardation or stunting of vegetative growth, sometimes characterized as reduction of stature.

Using the foregoing procedure, retardation of vegetative growth in excess of 25% was obtained with representative compounds of this invention at the equivalent rate of application indicated below.

| Compound of Example | Rate Lbs/Acre | Other Observed Modifications |
|---|---|---|
| 2 | 6.0 | Stimulation of axillary development; Altered canopy shape |
| 4 | 6.0 | Stimulation of axillary development; Altered canopy shape |
| 6 | 3.0 | Stimulation of axillary development |
| 7 | 6.0 | Stimulation of axillary development; Leaf alteration or distortion |
|  | 3.0 | Stimulation of axillary development; Leaf alteration or distortion; but no retardation |
|  | 1.2 | Stimulation of axillary development |

In other tests according to Example 8, the compounds of Example 3 and 5 effected no retardation of vegetative growth, but did result in stimulation of axillary development at 6.0 lb/ac. and, additionally for the compound of Example 5, the canopy shape was altered and slight leaf burn was noted; at 3.0 lb/ac., the latter compound also effected stimulation of axillary development.

The dark foliar color effect observed in tests for some of the compounds herein (see, e.g., Example 10, with respect to the compound of Example 2) results in a darker green plant and demonstrates higher chlorophyll activity indicative of improved rates of photosynthesis. Although additional tests were run at other rates of application, the rates recited above are indicative of the type of plant growth regulation obtained with the active ingredients of this invention when applied to plants at an early stage of growth.

The desirable plant growth regulating properties of the compounds of this invention are particularly unexpected since closely related compounds do not perform in the same manner. In tests conducted in accordance with Examples 8 and 9, 3-[(p-chlorophenyl)imino]-phthalide was found to be too active at the test rates between 2.5 and 6.0 lbs/acre, exhibiting moderate to severe herbicidal activity. However, this compound did exhibit stimulation of axillary development, leaf alteration and inhibition of apical development at these rates. Hence, at lower rates this compound may be a suitable plant growth regulator. Further, the components 3-[(p-methoxyphenyl)imino]-phthalide, 3-[(o-ethoxyphenyl)imino]-phthalide and the unsubstituted phenyl compound 3-[(phenyl)imino]-phthalide did not demonstrate any observed plant growth regulation and were categorized as inactive, thus demonstrating the criticality of the halo- and alkoxy-substituent groups and their positions on the phenyl ring.

EXAMPLE 9

In this evaluation soybean plants growing in individual pots which were 4 weeks old (3–4 trifoliate stage) and 6 weeks old (5–6 trifoliate stage) were used for each application of chemical. An overhead spray of the aqueous composition of the chemical is applied to 2 pots at each growth stage at an equivalent rate as indicated below. Two to four sets of plants which receive no chemical application are included and serve as controls. All of the pots are maintained under good growing conditions and are watered and are uniformly fertilized under uniform conditions. Two weeks after the application of the chemical the growth responses of the treated plants are compared with that of the control plants. The total height of the plant is measured to the tip of the terminal bud. A decrease of 15% or more in the average total height of the treated plants, when compared to that of the control plants, demonstrates that the chemical is effective for regulating the natural growth or development of the plants. In addition to this retardation of vegetative growth, other observations indicating a response in the plants treated with chemicals of this invention were noted.

Employing the above procedure, representative compounds of this invention were effective in reducing the total height of the plant in excess of 15% at the equivalent rate of application indicated below to the 4 and 6 week old plants.

| Compound of Example | Rate Lbs/Acre | Other Observed Modifications |
|---|---|---|
| 2 | 5.0 | No retardation or growth, but stimulation of pod set was affected |
| 2 | 5.0 (Duplicate) | Retardation of vegetative growth; Dark foliar color; Early pod set; Stimulation of pod set |
| 3 | 5.0 | Stimulation of pod set |
|  | 5.0 (Duplicate) | Altered canopy shape |
| 4 | 5.0 | Altered canopy shape; pod set |
|  | 5.0 (Duplicate) | Epinasty; altered canopy |
| 6 | 2.5 | Stimulation of pod set; Altered canopy shape; Delayed pod set |

As used herein "stimulation of pod set" connotes an increase in the number of seed pods and/or seeds. "Early pod set" and "delayed pod set" have reference to the normal flowering time of a plant; early pod set being premature and delayed being later.

EXAMPLE 10

In tests on other crop plants, an aqueous solution containing as the active ingredient the compound of Example 7 was tested in tomatoes. In tomatoes, generally treated when the second flower cluster is formed, but not yet open, it was noted that an altered canopy shape resulted at rates of 1.2, 3.0 and 6.0 lb/ac.; leaf alteration resulted at the 3.0 and 6.0 lb/ac. rates, but not at 1.2 lb/ac., although leaf distortion did occur at this lower rate. Leaf distortion connotes a modification of normal growth pattern associated with some leaf injury, whereas leaf alteration connotes a modified growth pattern not associated with leaf injury.

EXAMPLE 11

A water solution of the compound of Example 7 was applied to cotton at the onset of flowering. The application rates used were about 1.2, 3.0 and 6.0 pounds per acre of active ingredient. At 1.2 lb/ac. rate, this compound is inactive in cotton. At the 3.0 and 6.0 lb/ac. rates, no effect on the plant height of the treated plants was observed. At 3.0 lb/ac., the treated plants exhibited stimulation of axillary development and leaf distortion, while at 6.0 lbs/ac., the observed effects were stimulation of axillary development, altered canopy shape and a dark foliar color.

EXAMPLE 12

In field tests, plots of soybean plants (Wayne, Williams and Corsoy varieties) growing in 20 inch row spacings, and having a population density of 250,000 seeds/acre (11 seeds/row ft) were treated with a water solution of the compound of Example 2 at rates equivalent to 1.0, 0.5 and 0.25 pounds per acre of active ingredient.

Application volume was 30 gpa. Tween 20 (polyoxyethylene (20) sorbitan monolaureate) was used as surfactant with the compound of Example 2 (0.25% v/v).

The application of chemical was made to the plants when the plants were beginning to blossom, approximately 10% blooms. At harvest the treated plants were compared to untreated control plants growing under the same conditions of row spacing and population density. These treatments resulted in a reduction of height of the plants generally in excess of 15% without damage to the plant, an increase in seed size of the Wayne and Williams varieties, and a yield enhancement in all three varieties, with Corsoy and Wayne showing the greatest responses.

In utilizing the methods and compositions of this invention, it is often advantageous to treat the crops which are beginning to blossom in order to elicit a growth response to optimize the plants' efficiency in producing fruit.

The methods of this invention can be conveniently carried out in conjunction with agronomic practices such as treating the plants with insecticides, fungicides, nematocides, fertilizer and the like. The application of compositions containing an active ingredient as herein defined and other agricultural chemicals such as selective herbicides, insecticides, fungicides, fertilizers, nematocides and the like are particularly advantageous for obtaining the desired result with minimum treatment costs.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

We claim:

1. A method of regulating the natural growth or development of plants which comprises applying to the plants or soil a non-lethal amount of compound selected from those having the formula

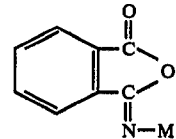

wherein M is selected from the group of radicals consisting of naphthyl, tolyl, o- and m-monochloro and monobromo and dichloro- and dibromophenyl, o, m-dimethoxyphenyl, and o-chloro- or bromo-m-trifluoromethylphenyl.

2. Method according to claim 1 wherein said plants are dicotyledons.

3. Method according to claim 2 wherein said dicotyledons are soybeans.

4. Method according to claim 2 wherein said dicotyledons are tomatoes.

5. Method according to claim 2 wherein said dicotyledons are cotton.

6. Method according to claim 2 wherein said dicotyledons are treated with 3-[(o-chloro-m-trifluoromethylphenyl)-imino]-phthalide.

7. Method according to claim 1 wherein said plants are monocotyledons.

8. Method according to claim 7 wherein said monocotyledons are corn.

9. Method according to claim 7 wherein said monocotyledons are treated with 3-[(o, m-dimethoxyphenyl)imino]-phthalide.

10. Method according to claim 1 wherein said compound is applied at a rate of from about 0.01 to 20.0 lbs/acre.

11. A composition comprising a plant growth regulating amount of a compound selected from the group consisting of 3-[(o-chloro-m-trifluoromethylphenyl)imino]-phthalide and 3-[(o, m-dimethoxyphenyl)imino]-phthalide and an adjuvant.

12. Composition according to claim 11 wherein said compound is 3-[(o-chloro-m-trifluoromethylphenyl)imine]-phthalide.

13. Composition according to claim 11 wherein said compound is 3-[(o, m-dimethoxyphenyl)imino]-phthalide.

14. Composition according to claim 11 which contains from about 0.1 to 80% by weight of said compound.

* * * * *